(12) United States Patent
Kempen et al.

(10) Patent No.: US 6,585,697 B2
(45) Date of Patent: Jul. 1, 2003

(54) BLUNT TIP CANNULA WITH ACCESS PIN

(75) Inventors: Paul Martin Kempen, Pittsburgh, PA (US); Michael J. Kerwin, St. Louis, MO (US); Alan B. Ranford, Creve Coeur, MO (US); Daniel A. Talonn, University City, MO (US); Richard L. Fiser, Kirkwood, MO (US)

(73) Assignees: Board of Supervisors of Louisiana State University and Agricultural and Mechanical College, Baton Rouge, LA (US); Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/757,258

(22) Filed: Jan. 9, 2001

(65) Prior Publication Data

US 2001/0004057 A1 Jun. 21, 2001

Related U.S. Application Data

(63) Continuation of application No. 08/990,923, filed on Dec. 16, 1997, now Pat. No. 6,206,858.
(60) Provisional application No. 60/032,716, filed on Dec. 16, 1996.

(51) Int. Cl.[7] .............................................. A61M 5/24
(52) U.S. Cl. ..................... 604/205; 604/411; 206/571
(58) Field of Search ............................... 604/205, 206, 604/239, 243, 244, 403, 411, 111, 414, 905; 206/223, 561, 564, 571, 570, 437–439, 363–370

(56) References Cited

U.S. PATENT DOCUMENTS

| | | | |
|---|---|---|---|
| 2,456,001 A | 12/1948 | Jones | 128/215 |
| 2,512,568 A | 6/1950 | Saffir | 128/215 |
| 2,842,126 A | 3/1958 | Brown | 128/218 |
| 2,855,929 A | 10/1958 | Hein | 128/221 |
| 3,067,742 A | 12/1962 | Linke et al. | 128/213 |
| 3,581,605 A | 6/1971 | Taylor | 81/3.49 |
| 3,650,393 A | 3/1972 | Reiss et al. | 206/63.2 |
| 3,729,032 A | 4/1973 | Tischlinger et al. | 141/2 |
| 3,940,003 A | 2/1976 | Larson | 215/247 |
| 4,074,426 A | 2/1978 | Brandt | 30/1.5 |
| 4,121,588 A | 10/1978 | Geiger | 128/218 R |
| 4,153,160 A * | 5/1979 | Leigh | 206/370 |
| 4,194,509 A * | 3/1980 | Pickering et al. | 128/350 R |
| 4,197,848 A | 4/1980 | Garrett et al. | 128/247 |
| 4,543,101 A | 9/1985 | Crouch | 604/411 |
| 4,595,102 A * | 6/1986 | Cianci et al. | 206/572 |
| 4,758,230 A * | 7/1988 | Rycroft | 206/366 |
| 4,767,416 A | 8/1988 | Wolf et al. | 604/239 |
| 4,838,877 A | 6/1989 | Massau | 604/272 |
| 4,840,621 A | 6/1989 | Larkin et al. | 604/29 |
| 4,878,903 A | 11/1989 | Mueller | 604/199 |

(List continued on next page.)

FOREIGN PATENT DOCUMENTS

WO    WO 90/12606    11/1990

OTHER PUBLICATIONS

Kempen, P.M., "Assessing blunt canulae as replacements for hypodermic needles during intravenous therapy: safety and utility," Infec. Control Hosp. Epidemiol., vol. 18, pp. 169–174 (1997).

Berry, A.J., "The use of needles in the practices of anesthesiology and the effect of a needleless intravenous administration system," Anesth. Analg., vol. 76, pp. 1114–9 (1993).

Primary Examiner—Michael J. Hayes
(74) Attorney, Agent, or Firm—Bonnie J. Davis; John H. Runnels (57) ABSTRACT

The present invention relates to an access device which is provided as part of the packaging of a blunt tip cannula or blunt tip cannula/syringe combination. The access device is preferably positioned within an elongate sheath which also protects the blunt tip cannula and which also includes an internal barrier which separates the distal end of the blunt cannula from the distal end of the access device and protects one of the access pin or blunt tip cannula from exposure or contamination while the other is being used.

6 Claims, 8 Drawing Sheets

U.S. PATENT DOCUMENTS

| | | | |
|---|---|---|---|
| 5,020,220 A | 6/1991 | Miyake et al. | 30/2 |
| 5,047,021 A | 9/1991 | Utterberg | 604/283 |
| 5,062,836 A | 11/1991 | Wendell | 604/167 |
| 5,071,413 A | 12/1991 | Utterberg | 604/283 |
| 5,158,554 A | 10/1992 | Jepson et al. | 604/283 |
| 5,163,554 A * | 11/1992 | Lampropoulos et al. | 206/363 |
| 5,171,234 A | 12/1992 | Jepson et al. | 604/283 |
| 5,199,948 A | 4/1993 | McPhee | 604/86 |
| 5,207,699 A | 5/1993 | Coe | 606/182 |
| 5,209,735 A * | 5/1993 | Lazarus | 600/434 |
| 5,211,638 A | 5/1993 | Dudar et al. | 604/283 |
| 5,215,537 A | 6/1993 | Lynn et al. | 604/244 |
| 5,279,576 A | 1/1994 | Loo et al. | 604/187 |
| 5,351,383 A | 10/1994 | Behnke et al. | 29/430 |
| 5,354,275 A | 10/1994 | Behnke et al. | 604/86 |
| 5,354,537 A | 10/1994 | Moreno | 422/100 |
| 5,382,241 A | 1/1995 | Choudhury et al. | 604/192 |
| 5,400,500 A | 3/1995 | Behnke et al. | 29/785 |
| 5,403,283 A | 4/1995 | Luther | 604/164 |
| 5,411,499 A | 5/1995 | Dudar et al. | 604/411 |
| 5,433,330 A | 7/1995 | Yatsko et al. | 215/247 |
| 5,470,327 A | 11/1995 | Helgren et al. | 604/411 |
| 5,520,657 A | 5/1996 | Sellers et al. | 604/191 |
| 5,529,189 A | 6/1996 | Feldschuh | 206/570 |
| 5,549,577 A | 8/1996 | Siegel et al. | 604/256 |
| 5,580,351 A | 12/1996 | Helgren et al. | 604/411 |
| 5,807,374 A | 9/1998 | Caizza et al. | 604/411 |
| 5,820,621 A | 10/1998 | Yale et al. | 604/411 |

* cited by examiner figure 1 figure 2 figure 3 figure 4 figure 5 figure 6 figure 7 figure 8 figure 9 figure 10 figure 11 figure 14 figure 15 figure 16 figure 17

US 6,585,697 B2

BLUNT TIP CANNULA WITH ACCESS PIN

This is a continuation of application Ser. No. 08/990,923, filed Dec. 16, 1997, now U.S. Pat. No. 6,206,858, which claims the benefit of the Dec. 16, 1996 filing date of application Ser. No. 60/032,716 under 35 U.S.C. §119(e).

BACKGROUND

1. Field of the Invention

The present invention relates generally to an access device for a blunt tip cannula. More specifically, the present invention relates to a packaging combination of a blunt tip cannula and access device which maximizes the convenience to the user.

2. Background of the Invention

Medical containers such as medication vials are commonly used to store bulk quantities of medications in a sterile condition prior to use. Most often, these vials allow access to their contents through a septum made of a relatively thick, elastomeric material. The thick septum is designed to be pierceable by a sharp needle to allow access to the vial contents and to reseal after the needle is withdrawn. The thickness of the septum allows it to maintain its integrity even after multiple uses.

Medical tubing, such as IV tubing, often includes injection sites to allow medication or other fluid to be injected into the IV line. These injection sites often include an injection port which is also sealed with a relatively thick elastomeric septum which is intended to be pierced by a sharp needle.

Due to the relative thickness and general manufacturing specifications of these elastomeric septa, they are very difficult to pierce without a piercing element which includes a sharp tip. It is nevertheless becoming increasingly common, due to the problem with the potential spread of disease by accidental sticking with sharp tip needles, for users to attempt piercing septa with cannulas having blunt tips thereon. However, a problem arises when the septa are not pre-pierced. The blunt tip cannulas are not capable of puncturing through the septum material without prior piercing thereof with a sharp needle.

There has therefore existed in the art since the advent of the blunt tip cannula, a need for a device that facilitates penetrating the septum of a vial or an injection port to permit access with a blunt tip cannula.

An early prior art approach to resolving this problem has been to provide a vial adaptor which can be attached directly to the vial in such a way that the adaptor passes through the vial septum and is itself designed to allow a blunt tip cannula to pass therethrough in a facile manner. Examples of this concept have taken several different forms, such as disclosed in U.S. Pat. No. 5,433,330 to Yatsko et al., U.S. Pat. No. 3,940,003 to Larson and U.S. Pat. No. 4,543,101 to Crouch.

Another prior art attempt to solve the problem of accessing a vial or injection port septum with a blunt tip cannula has been to merely pre-pierce the septum to provide a path through which the blunt tip cannula may pass. This has been done by pre-piercing the vial or injection port septum with a sharp pin or needle just prior to penetrating with the blunt tip cannula. However, these solutions have been less than completely desirable. Vial adaptors require additional significant time in setting up or changing over the vial for blunt cannula access. Also, septa pre-pierced at the time of assembly are often difficult to identify visually. Pre-piercing a septum with a sharp needle and syringe just prior to inserting a blunt tip cannula therethrough has the dual draw back of requiring the use of a sharp needle, which is what the blunt tip cannula is designed to avoid, and the added expense of using two needle systems, a sharp tip needle and the blunt tip cannula, to accomplish vial or injection port access.

Finally, another prior art approach utilizes a pointed adaptor provided at the tip of a cannula for piercing the injection port septum. U.S. Pat. Nos. 5,470,351 and 5,580,351, to Helgren et al. disclose a device comprising a blunt tip cannula with a pointed adaptor at the distal end thereof for piercing the septum and subsequently permitting entry of the blunt tip cannula therethrough. However, the pointed adaptor utilized in the Helgren et al. device includes a breakaway collar that leaves the pointed adaptor inside the vial after the septum has been pierced which is undesirable. Therefore, there is a need in the art for providing an access device for piercing the septum of a vial and providing it as part of the packaging of a blunt tip cannula or blunt tip cannula/syringe combination which overcomes the drawbacks of the prior art.

OBJECTS AND SUMMARY OF THE INVENTION

It is an object of the present invention to provide an access device that assists the placement of a blunt tip cannula into a septum.

It is another object of the present invention to provide an access device which is conveniently packaged in combination with a blunt tip cannula.

It is further an object of the present invention to provide a blunt tip cannula and access device which are packaged together in a manner which is economical to manufacture, easy to use, and limits the possibility of an accidental stick.

Briefly, and in general terms, the present invention solves the above-identified problem of vial access for a blunt tip cannula by providing a vial access device/blunt tip cannula combination which is designed and packaged in a manner which allows for convenient use.

In a presently preferred embodiment, given by way of example and not necessarily by way of limitation, a blunt tip cannula and access device according to the principles of the present invention may include a syringe-mounted blunt tip cannula which is protected by an elongate hollow sheath into which the distal end of the cannula is inserted for protection prior to use. The sheath extends beyond the distal end of the blunt tip cannula and also receives the sharp distal tip of an access pin. The access pin includes a finger grip or handle section which extends from the distal end of the sheath when the sharp tip thereof is positioned therein, and facilitates easy removal of the pin from the sheath for use. The hollow section of the sheath is preferably bifurcated by an internal barrier which prevents fluid communication between the blunt tip cannula and the access pin and thus protects the cannula and the access pin from contamination when one or the other is removed from the sheath for use.

A similar combination of blunt-tip cannula, access device and sheath may be employed without a syringe, by providing a protective cap over the proximal end of the sheath to completely enclose the blunt tip cannula, so that the combination may be packaged and shipped separately from the syringe.

In a preferred embodiment of the invention, the access pin and blunt tip cannula are positioned within the sheath so that each is oriented along a single longitudinal axis, with the distal end of the cannula being directed toward the distal end of the access pin, with the two being separated from one another by the sheath's internal barrier. This orientation simplifies use of the device by allowing the user to grasp one end of the sheath and the blunt tip cannula with one hand and the opposite end of the sheath and the access pin with the other hand and immediately withdraw either the blunt tip cannula or the access pin as desired from the sheath with one easy movement, and without being subjected to the possibility of an accidental stick.

The above and other objects and advantages of the present invention, including alternative embodiments thereof, will become apparent from the following more detailed description, when taken in conjunction with the accompanying drawings in which like elements are identified with like numerals throughout.

DETAILED DESCRIPTION OF THE PREFERRED EMBODIMENTS

As shown in the exemplary drawings for the purpose of illustration, an embodiment of a package for a blunt tip cannula and access pin made in accordance with the principles of the present invention, referred to generally by the reference numeral 10, is provided for simple and rapid pre-piercing of a septum such as commonly used on a medication vial or an IV injection port (not shown), prior to insertion of a blunt tip cannula 20 therethrough to obtain or inject fluid.

Figure 1:
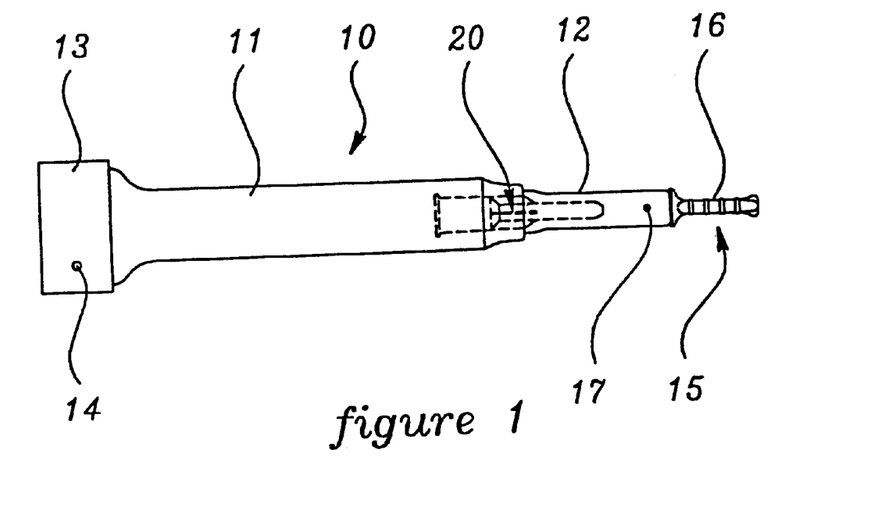
FIG. 1 is a side view of a packaged blunt tip cannula and access pin of a preferred embodiment of the present invention.
Figure 2:
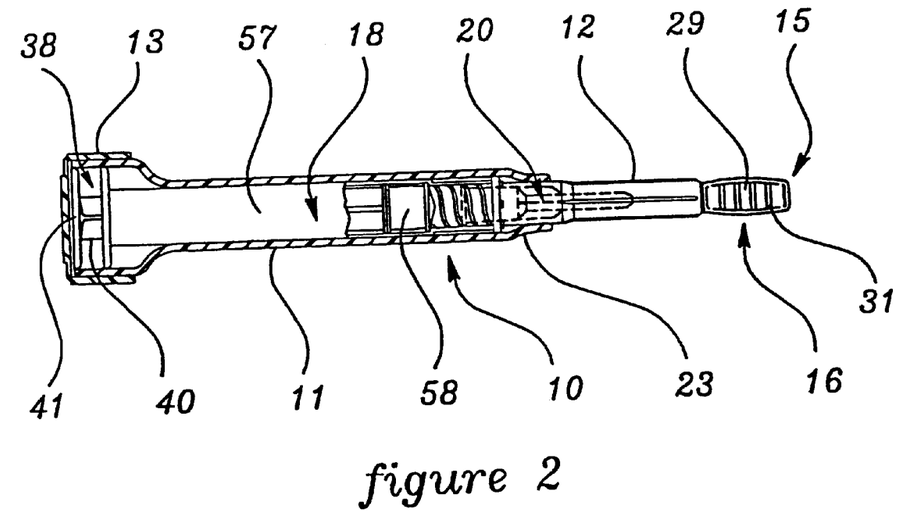
FIG. 2 is a cut-away view of the packaged blunt tip cannula and access pin of a preferred embodiment of the present invention.

More specifically, as shown in FIGS. 1 and 2, a package 10 is shown which is designed to completely contain a sterile syringe 18 and blunt tip cannula 20, and to retain an access pin 15 protected against contamination and accidental sticking. The syringe 18 comprises a hollow barrel 57 and a plunger 38. The plunger 38 includes a plunger tip 58 and a plunger rod 40 connected to the tip 58. The plunger tip 58 is slidably positioned within the barrel 57 in sealing contact with the inside surface of the barrel 57. The rod 40 extends out of the barrel 57 and facilitates movement of the tip 58 by manipulation of the rod 40 outside the barrel 57. The rod 40 includes a flange 41 for convenient pushing or pulling of the rod 40 by the fingers of a user.

The package 10 includes a sleeve 11 which is open at its distal end to allow protrusion therethrough of the sheath 12, and open at its proximal end to allow removal of the syringe/sheath assembly. The package 10 finally includes a cap 13 which closes the proximal opening of the sleeve 11 and which is preferably affixed to the sleeve 11 by tamper-evident means such as a heat stake 14 as is well known in the art. The access pin 15 is positioned in the distal end of the sheath 12 such that the handle 16 thereof protrudes from the sheath's distal end. The access pin 15 is also preferably held in position within the sheath 12 by means of a heat stake 17. The blunt tip cannula 20 (see FIGS. 3 and 15) has a tip extension 44 that forms a cannula bore 43 along the longitudinal axis of cannula 20 with an attachment portion or hub 45 at the proximal end thereof adapted for securing the blunt cannula 20 to the distal end of syringe 18.

When it is desired to remove the syringe 18 from the package 10, the heat stake 14 is broken and cap 13 is removed from the sleeve 11. The entire sheath 12, access pin 15, blunt tip cannula 20 (see FIG. 3), and syringe 18 may then be withdrawn from the sleeve 11. Once removed from the sleeve 11, the user, as desired, either breaks the heat stake 17 and removes the access pin 15 from the sheath 12 to pre-pierce the septum of a vial or an IV access port, or alternatively withdraws the blunt tip cannula 20 (see FIG. 3) from the proximal end of the sheath 12 for immediate use.

Figure 3:
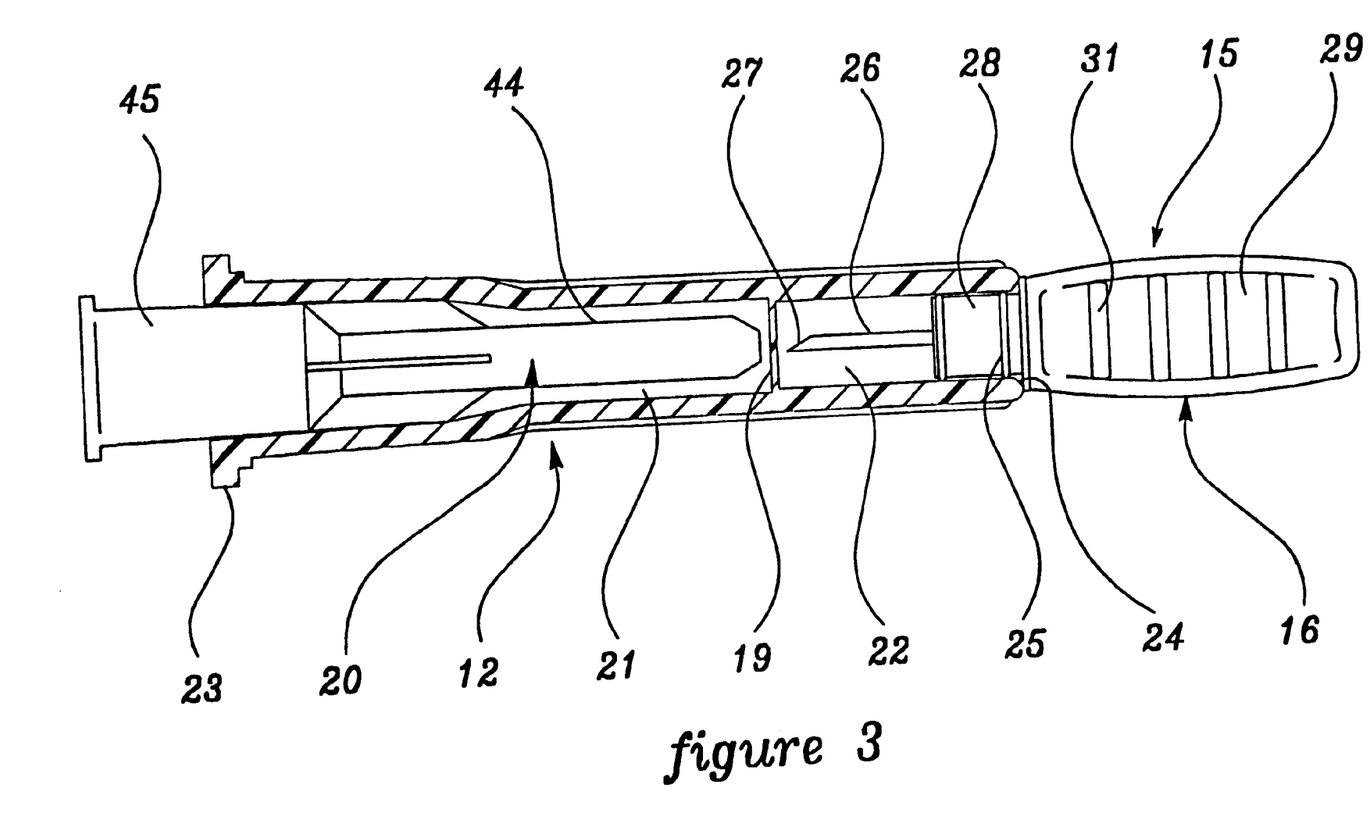
FIG. 3 is a partial cross-sectional view of a blunt tip cannula and access pin positioned in a sheath formed in accordance with a preferred embodiment of the present invention.

As shown in FIG. 3, the blunt tip cannula 20 and the access pin 15 with a sharp distal tip 27 are mounted in the sheath 12 for use. The sheath 12 is generally hollow, and is preferably bifurcated into two separate hollow sections 21 and 22 by an internal barrier 19. The hollow sections 21 and 22 of the sheath 12 are specifically designed to receive the blunt tip cannula 20 and access pin 15 respectively, primarily in a friction fit relationship. The sheath 12 may also include a flange 23 which has a diameter slightly larger than the distal opening of the sleeve 11 in order to prevent the sheath 12 from passing completely therethrough when assembled with the sleeve 11. Also, if desired, the sheath 12 may include an internal rib 24 which can cooperate with an annular protruding rib 25 on the access pin 15 to cause the pin 15 to be seated in the hollow section 22 in a snap-fit manner.

Figure 4:
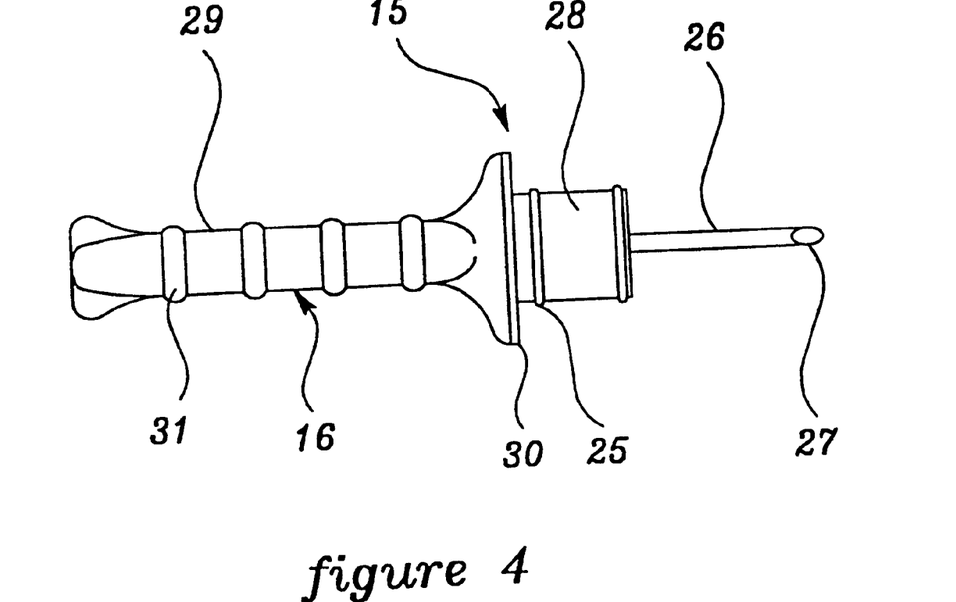
FIG. 4 is a side view of an access pin formed in accordance with the present invention.
Figure 5:
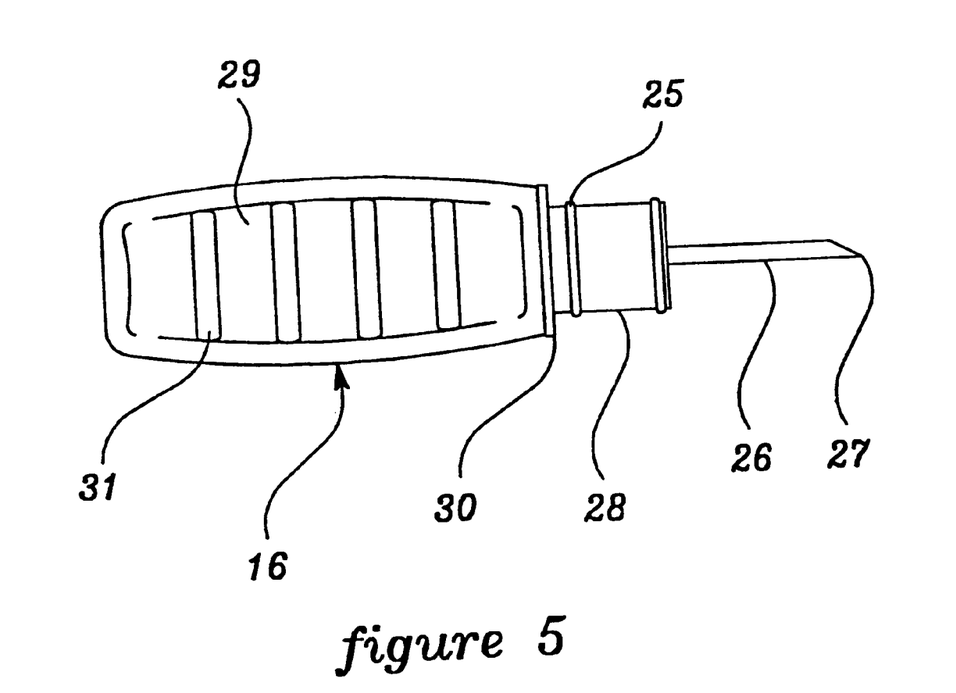
FIG. 5 is a side view of the access pin of FIG. 4 rotated 90° along its longitudinal axis.

Referring to FIGS. 4 and 5, the access pin 15 preferably includes an elongate pin 26 having a sharpened, or otherwise pointed distal tip 27. The proximal end of the pin 26 is removably embedded in the handle 16 which includes a hub portion 28 and finger gripping portion 29. The finger gripping portion 29 includes an enlarged flange element 30 which abuts against the distal end of the sheath 12 when the pin 15 is properly positioned therein prior to use. The hub 28 is preferably sized to equal the diameter of the hollow section 22 of the sheath 12 to improve its friction fit therewith when assembled. If desired, the handle 16 may be formed into a relatively flat configuration and include gripping ridges 31 to improve the user's ability to securely grip the handle 16 with the fingers and the thumb.

FIGS. 6-9 show alternative embodiments of the combination of the access pin 15, blunt tip cannula 20 and sheath 12 in their assembled/packaged configuration. Each of these alternative embodiments includes the general concept of packaging the sharp access pin 15 in such a way as to prevent accidental sticks, while at the same time allowing independent use of either the access pin 15 or the blunt tip cannula 20 while leaving the other protected by the sheath 12, without exposure to non-sterile conditions. Further, each includes the general concept of positioning the access pin 15 and blunt tip cannula 20 along a single longitudinal axis which allows the user to separate one or the other from the sheath 12 in a single, safe, two-handed withdrawing motion which substantially avoids the possibility of an accidental stick or an unwanted contamination.

Figure 6:
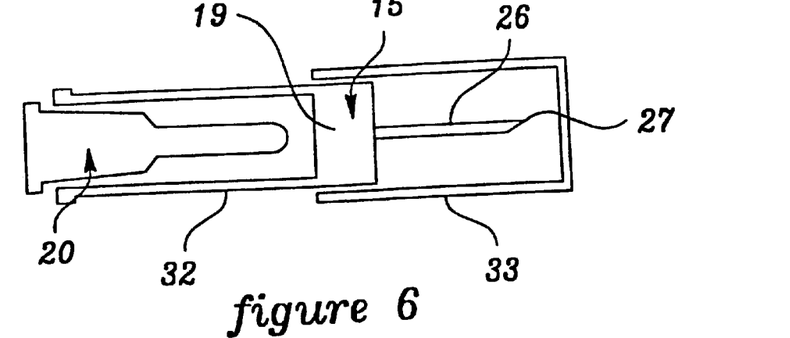
FIGS. 6–9 are cross-sectional views of alternative embodiments of the packaging combination of the blunt tip cannula, access pin and protective sheath in accordance with the present invention.

Referring specifically to FIG. 6, the access pin 15 has been modified to include a partial sheathing member 32 which covers the blunt tip cannula 20. The distal tip 27 of the access pin 15 is then covered with the modified sheath 33.

Figure 7:
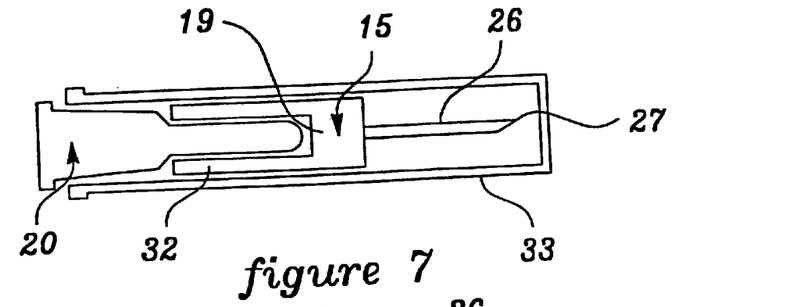

Referring specifically to FIG. 7, the access pin 15 has been modified in a manner similar to that described above with respect to FIG. 6, except that the modified sheathing member 33 extends to cover the access pin 15 entirely and also the blunt tip cannula 20.

Figure 8:
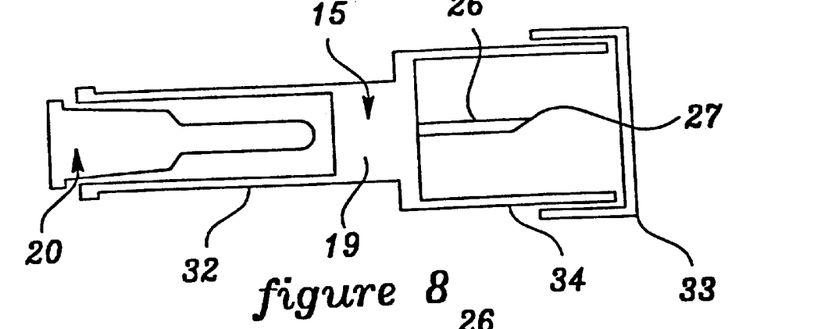

Referring specifically to FIG. 8, the access pin 15 has been further modified to include a secondary partial sheathing member 34 which extends beyond the distal tip 27 of the pin 15. The modified sheath member 33 then merely covers the open end of the secondary partial sheathing member 34. This secondary partial sheathing member 34 can be sized to fit over the neck of a medication vial and/or the end of an IV access port, to allow the tip 27 of the pin 15 to pierce the septum.

Figure 9:
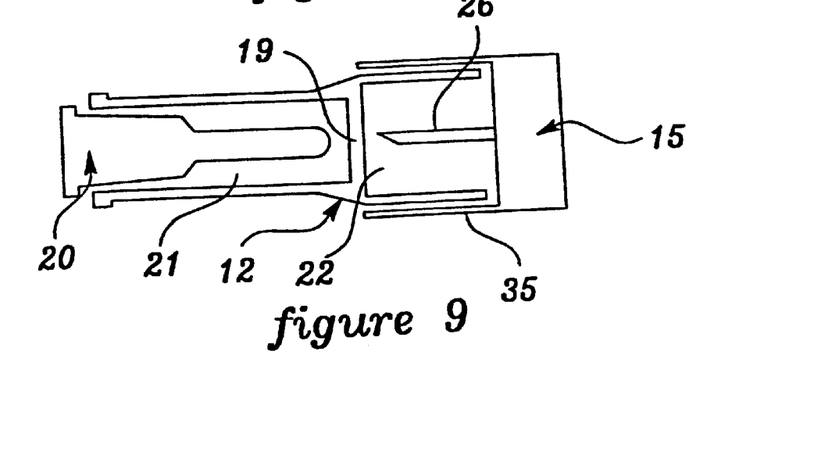

Referring specifically to FIG. 9, the sheath 12 operates again in a manner very similar to the preferred embodiment shown in FIG. 3, except that the access pin 15 does not include a hub which friction fits with the internal wall of the hollow section 22, but instead includes an exterior extension 35 which fits over the exterior surface of the sheath 12. The embodiments of both FIGS. 8 and 9 include the added feature of protecting the distal tip 27 of the access pin 15 from accidental sticks even when the pin 26 is removed from the sheathing system.

Figure 10:
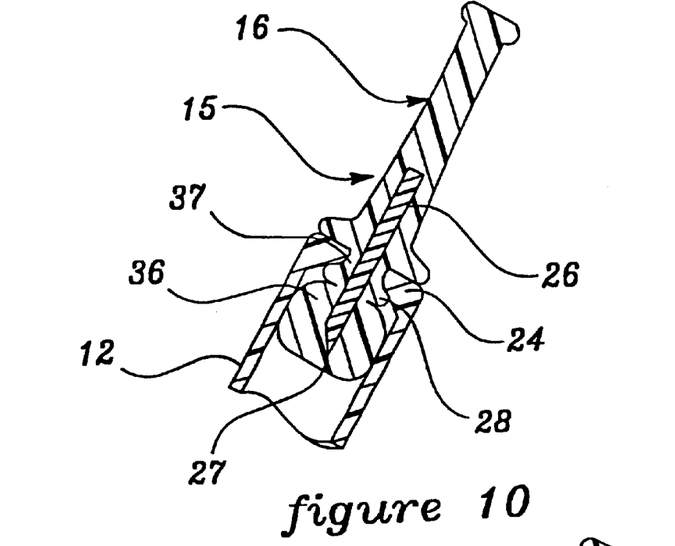
FIG. 10 shows a cross-sectional view of an alternative embodiment of the access pin which includes a shearing cap thereon.
Figure 11:
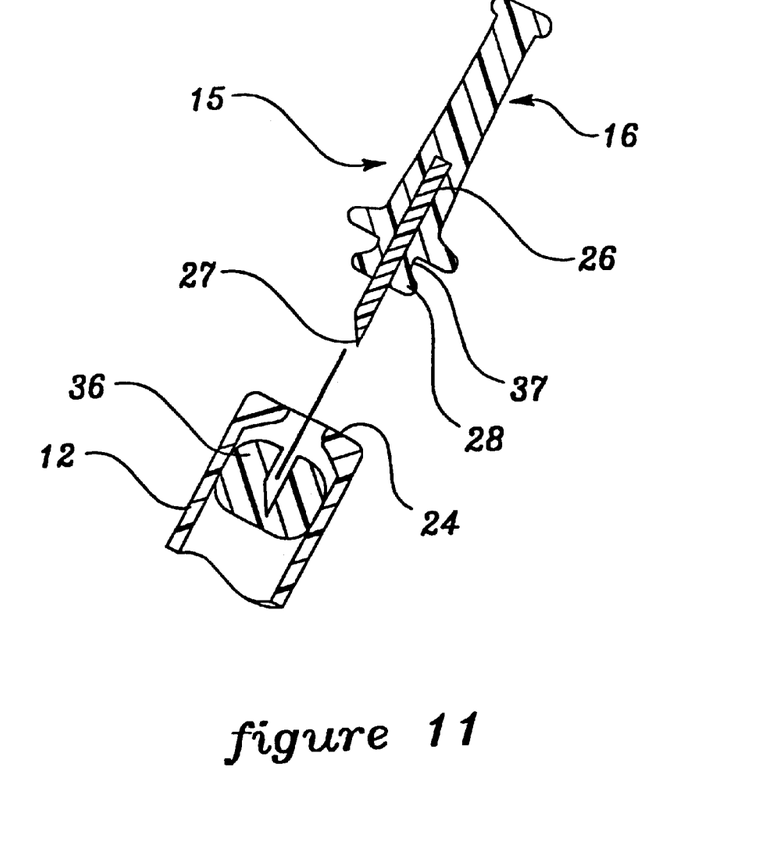
FIG. 11 shows a cross-sectional view of the access pin of FIG. 10 removed from the shearing cap.

FIG. 10 shows another alternative embodiment of the present invention which includes a shearing cap 36 which is formed as part of the access pin 15. In this embodiment, the sheath 12 need not have a separate internal barrier 19, since the shearing cap 36 serves the same function. The shearing cap 36 can be formed as part of the handle 16 such that it must be broken away from the handle 16 when the access pin 15 is removed from the sheath 12 for use. As shown in FIG. 11, removal of the access pin 15 leaves the shearing cap 36 in place within the sheath 12.

Also in reference to the alternative embodiment shown in FIGS. 10 and 11, the hub 28 of the handle 16 may be modified to include a groove 37 which operates in conjunction with an internal rib 24 of the sheath 12 to hold the access pin 15 in place within the sheath 12. When he access pin 15 is removed from the sheath 12, the enlarged internal rib 24 constricts the opening in the sheath 12 to a diameter sufficiently small that the hub 28 of the access pin 15 cannot be reinserted, thus operating as a non-resheathability feature as well as a tamper-evident indication. If desired, other tamper-evident features may be added such as a shrink wrap polymeric film which can be wrapped around a portion of the sheath 12 and the access pin 15 and which is subsequently partially destroyed upon removal of the access pin 15 from the sheath 12.

Figure 12:
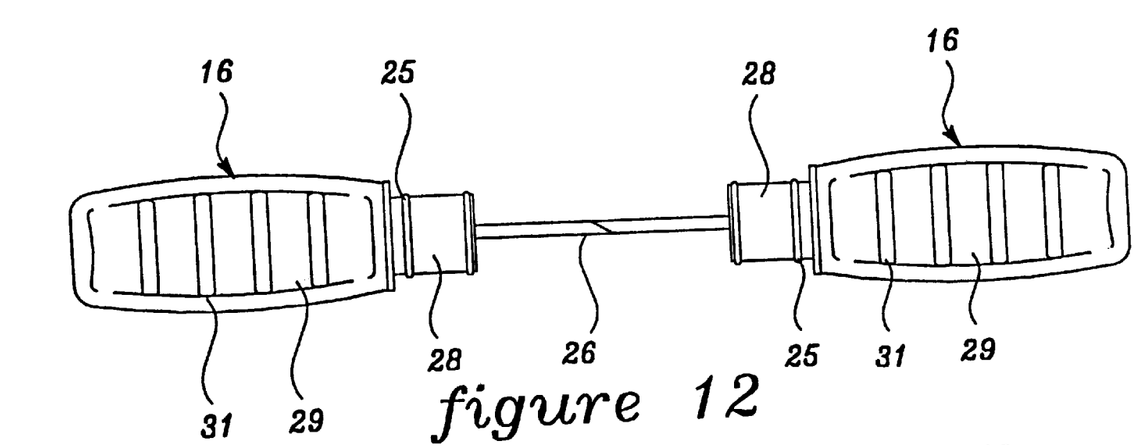
FIG. 12 shows a side view of a pair of access pins joined as a doublet just prior to completion of the final manufacturing step to form two separate access pins.
Figure 13:
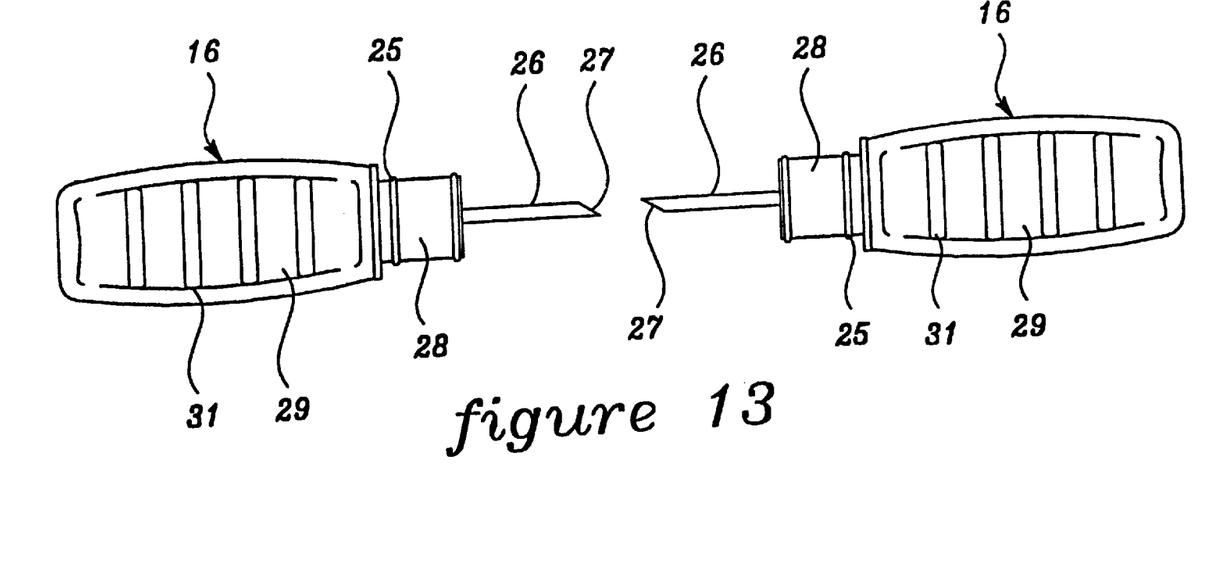
FIG. 13 shows a side view of the doublet access pins of FIG. 12 after the final manufacturing step has been completed.

As shown in FIG. 12, a preferred method of manufacturing access pin 15 is to form a double-length piece of pin 26 and to mold a handle 16 on each end thereof. Then, as shown in FIG. 13, the double length pin 26 is clipped at its center with an angled cut to form two finished access pins 15.

When used to pre-pierce a septum, the present invention as shown in FIG. 1 is held by the user with both hands so that the fingers of one hand are holding the handle 16 of the access pin 15 and the other hand is holding the remainder of the device. The access pin 15 is then pulled away from the sheath 12 and the remainder of the device is set aside. The user then pierces the septum of a vial or IV access port (not shown) with the access pin 15 and immediately discards the access pin 15 into an appropriate "sharps" container. Thereafter, the user removes the cap 13 and sleeve 11 from the syringe 18, and withdraws the blunt tip cannula 20 from the sheath 12. The blunt tip is then inserted through the pre-pierced septum into the vial or IV line and fluid is withdrawn or injected as desired.

Alternatively, if a septum has already been pre-pierced, either through previous use, or other pre-piercing methods, the user may leave the access pin 15 safely engaged within the sheath 12 and instead immediately remove the syringe 18 and blunt tip cannula 20 from the sleeve 11 and sheath 12 respectively, and insert the blunt tip cannula into the vial for removal of fluid. In either method of use, the access pin 15 or blunt tip cannula 20 remain protected at all times prior to use.

Figure 14:
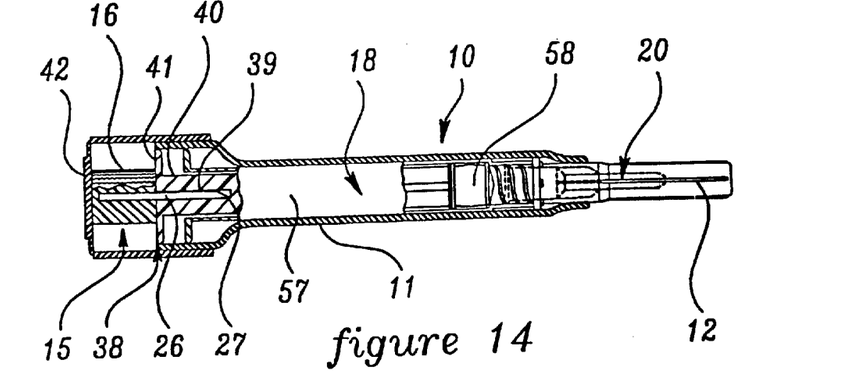
FIG. 14 shows a cut-away view of an alternative embodiment of the blunt tip cannula and access pin packaged with the distal tip of the access pin inserted in a small bore in the plunger rod of a syringe.

Referring to FIG. 14, in an alternative embodiment the access pin 15 is removably embedded or otherwise inserted inside a plunger rod bore 39 formed at the proximal end of plunger 38 for securely attaching access pin 15 thereto. An enlarged cap 42 is provided for secure attachment, for example friction or snap fit engagement, around the proximal end of sleeve 11 in such a manner that the sterility of the access pin 15 and the rest of package 10 are maintained.

Figure 15:
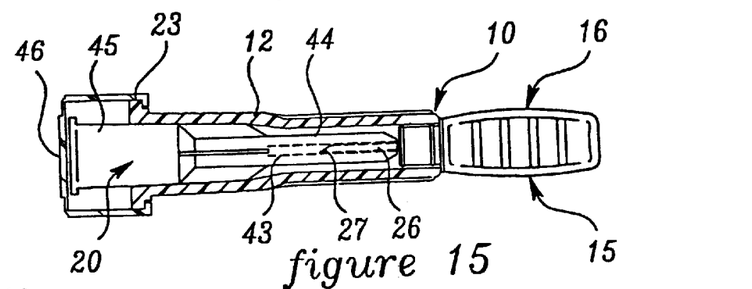
FIG. 15 is a partial cross-sectional view of an alternative embodiment of the blunt tip cannula and access pin packaged with the distal tip of the access pin positioned within the bore of the blunt tip cannula.

As shown in FIG. 15, in another alternative arrangement, the distal tip 27 of the access pin 15 is positioned inside the distal end of bore 43 of the blunt tip cannula 20. As described above, the access pin 15 is secured to the distal end of sheath 12 in a friction fit relationship thereto, while a sheath cap 46 is engaged over the flange 23 for enclosing the proximal end of access pin 15 and maintaining the sterility of the blunt tip cannula 20 and access pin 15 inside sheath 12.

Figure 16:
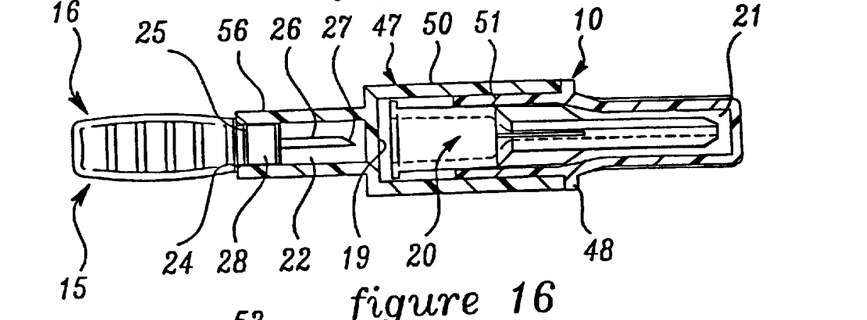
FIG. 16 is a partial cross-sectional view of an alternative embodiment of the blunt tip cannula and access pin packaged with the distal tip of the access pin isolated from the blunt tip cannula in a separate sheath.

FIG. 16 shows another alternative arrangement of the blunt tip cannula 20, access pin 15 and a modified protective sheath 51 with barrier 19 forming two hollow sections 21 and 22, respectively. As noted in the embodiment illustrated in FIG. 3, barrier 19 provides a sterile seal that separates the blunt tip cannula 20 from the access pin 15, so that either the cannula 20 or the access pin 15 may be removed from package 10 without compromising the sterility of the other. In this arrangement access pin 15 is attached to a second sheath portion 56 of a secondary sheath member 47 in a friction fit engagement thereto, whereby sheath member 47 includes an enlarged rib 24 which is adapted to cooperate with the annular protruding rib 25 formed around the hub portion 28 of pin 15. This friction fit engagement between the access pin 15 and the secondary sheath member 47 maintains the sterility of the access pin 15 inside hollow portion 22. As further illustrated in FIG. 16, secondary sheath member 47 further includes a first sheath portion 50 that is adapted to engage a modified sheath 51 in a friction fit engagement thereto so that sterility of the blunt tip cannula 20 is maintained. A flange 48 is provided around the middle portion of modified sheath 51 for engaging first sheath portion 50. In an alternative embodiment to that shown in FIG. 16, barrier 19 may be removed and the access pin 15 spaced apart from blunt tip cannula 20.

Figure 17:
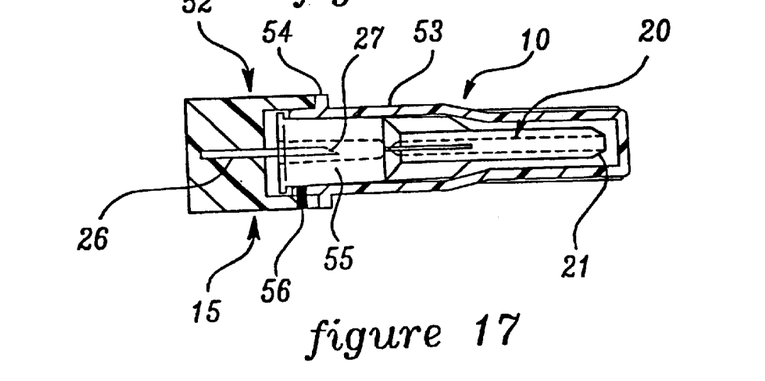
FIG. 17 is a partial cross-sectional view of an alternative embodiment of the blunt tip cannula and access pin packaged with the access pin formed as part of a cap positioned on the blunt cannula sheath.

Another alternative arrangement of the blunt tip cannula 20, access pin 15 and a modified protective sheath 53 is shown in FIG. 17. In this arrangement, access pin 15 has a modified handle 52 which serves to enclose access pin 15 and for which is adapted for attachment to the proximal end of modified sheath 53. Sheath 53 has been modified to include an annular flange 54 which abuts the modified handle 52 when handle 52 is attached in a friction fit engagement to the proximal end of sheath 53. With the access pin 15 engaged to the proximal end of sheath 53, the distal tip 27 of pin 15 is positioned inside a hollow interior portion 55 of the blunt tip cannula 20. In this configuration, the handle 52 of the access pin 15 provides a means for encapsulating the access pin 15 and blunt tip cannula 15 inside package 10 in a sterile environment. A heat stake 56 may also be provided as a tamper-evident indication for package 10.

Figure 18:
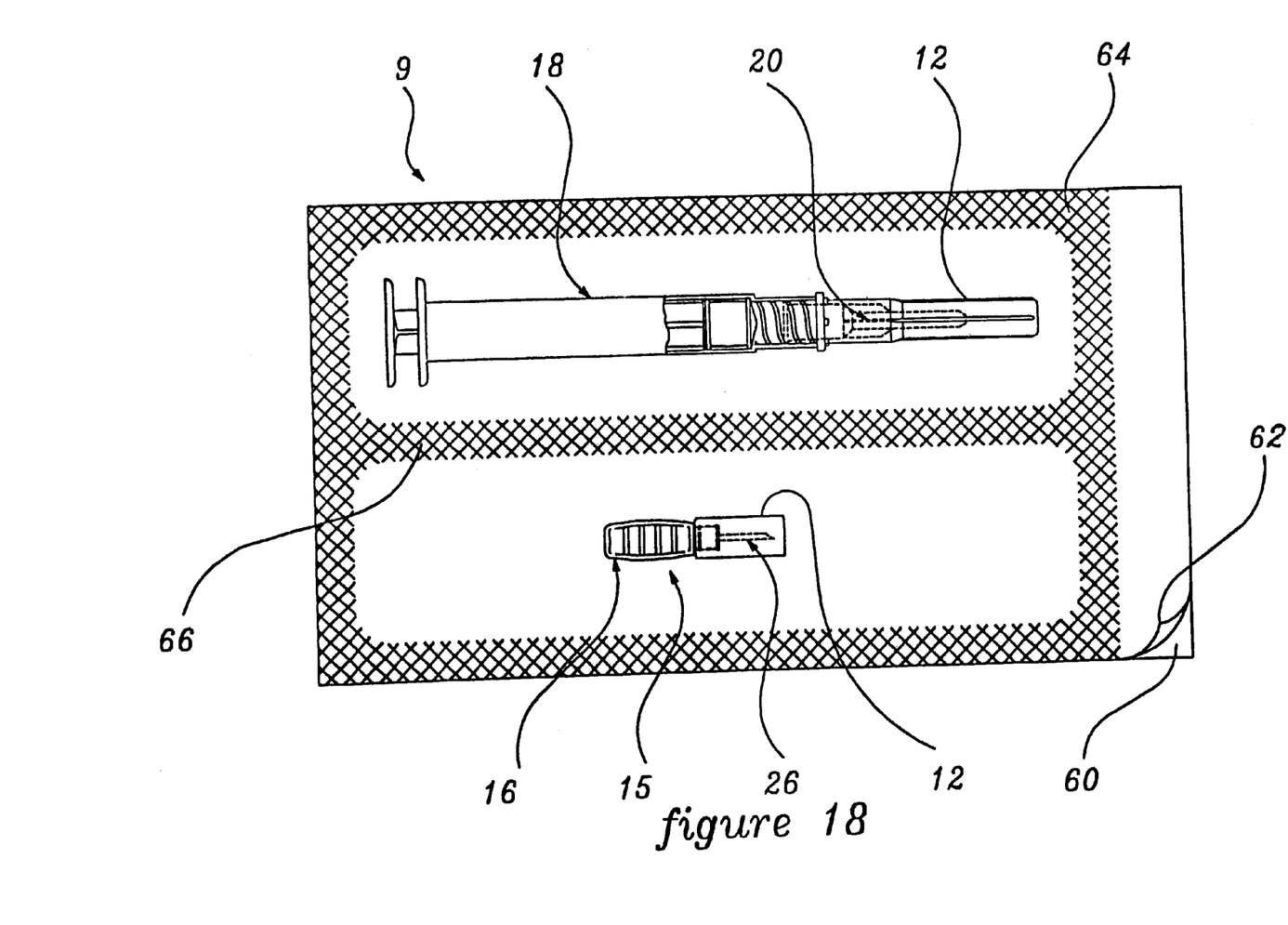
FIG. 18 is a cross-sectional view of the access pin separated from the blunt tip cannula/syringe combination inside the same shipping package.

As shown in FIG. 18, a sterile package 9 may be utilized instead of the hardpack sterile package 10 shown in FIGS. 1–17. Although FIG. 18 shows a softpack package 9 for a syringe 18 and blunt cannula/syringe combination 18 and 20 (see FIGS. 1, 2, and 14) and associated access pin 15, a similar packaging arrangement could also be used for a blunt cannula 20 and associated access pin 15 without a syringe 18 (see FIGS. 3, 6–9, 15–17). The access pin 15 is packaged separately from, but associated with, the blunt tip cannula 20 preattached to the syringe 18 in the same sterile package 9. The blunt cannula/syringe combination 18 and 20 and access pin 15 are sandwiched between a treated paper or Tyvek® backing 60 and a film 62, such as a Mylar® polyethylene laminate. The backing 60 and film 62 are sealed along sealing line 64 with heat or adhesive around the periphery of the package 9 outside the articles contained therein to form a sterile barrier around the articles therein. As shown in FIG. 18, the blunt cannula/syringe combination 18 and 20 may be isolated from the access pin 15 with a seal line 66 extending from one end of the package to the other at the peripheral seal line 64 between the cannula/syringe combination 18 and 20 and the access pin 15 in order to maintain the sterile conditions of both devices. Alternatively, the seal line 66 could be omitted to position the access pin 15 and cannula 20 in the same sealed sterile package. Alternatively, the syringe 18, cannula 20 and access pin 15 could be loosely enclosed in a common sterile package 9 in association with one another, or separate sterile packages 9 connected together could be employed. Other packaging systems may be employed to package medical devices in sterile enclosures, including, without limitation, thermoformed plastic trays with Tyvek® polyethylene laminate covering a tray adapted to contain the cannula 20, syringe 18 and access pin 15 in association with one another in accordance with the principles of the present invention.

The different configurations of sheath 12 shown in FIGS. 1–3, 6–9 and 14–18 may be collectively referred to as a "sheathing system", while the different packages 9 and 10 may be referred to as a "packaging system". Further, access pin 15 may be referred to as an "access device" and packages 9 and 10 may be referred to as a "packaging device".

The complete disclosures of all references cited in this specification are hereby incorporated by reference. Also incorporated by reference is the full disclosure of the following unpublished document: U.S. Provisional Application 60/032,716 entitled "Blunt Tip Cannula With Access Pin". In the event of an otherwise irreconcilable conflict, however, the present specification shall control.

It will be apparent from the foregoing that, while particular embodiments of the invention have been illustrated and described, various modifications can be made thereto without departing from the spirit and scope of the invention. Accordingly, it is not intended that the invention be limited, except as by the appended claims.

What is claimed is:

1. In combination, a blunt tip cannula and an access device comprising:

a blunt tip cannula, an access device for pre-piercing a septum, a packaging device for protecting said blunt tip cannula and said access device when said blunt tip cannula and said access device are assembled therewith for storage, wherein at least one of said access device and said blunt tip cannula can be removed from said packaging device independently of the other of said access device and blunt tip cannula, wherein said packaging device further includes a barrier that segregates the access device from the blunt tip cannula, wherein said blunt tip cannula and said access device are oriented along a single longitudinal axis when assembled to said packaging device, and wherein said pin of said access device is removably embedded in said barrier when said access device is assembled to said packaging device.

2. The combination according to claim 1 wherein said packaging device includes a tamper-evident attachment mechanism for said access device.

3. The combination according to claim 2 wherein said tamper-evident attachment mechanism is a heat stake.

4. The combination according to claim 2 wherein said tamper-evident mechanism includes a shrink wrap polymeric film positioned around at least a portion of said access device when said access device is assembled to said packaging device.

5. In combination, a blunt tip cannula and an access device comprising:

a blunt tip cannula, an access device for pre-piercing a septum, a packaging device for protecting said blunt tip cannula and said access device when said blunt tip cannula and said access device are assembled therewith for storage, wherein at least one of said access device and said blunt tip cannula can be removed from said packaging device independently of the other of said access device and blunt tip cannula, wherein said packaging device further includes a barrier that segregates the access device from the blunt tip cannula, and wherein said packaging device includes an interference member which prevents reassembly of said access device to said packaging device.

6. The combination according to claim 5, wherein said interference member includes an annular internal rib on said packaging device which interferes with reattachment of said access device to said packaging device.

\* \* \* \* \*